(12) United States Patent
Yamaguchi et al.

(10) Patent No.: US 7,095,884 B2
(45) Date of Patent: Aug. 22, 2006

(54) METHOD AND APPARATUS FOR CIRCUIT PATTERN INSPECTION

(75) Inventors: Atsuko Yamaguchi, Kodaira (JP); Tsuneo Terasawa, Ome (JP); Tadashi Otaka, Hitachinaka (JP); Takashi Iizumi, Hitachinaka (JP); Osamu Komuro, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 547 days.

(21) Appl. No.: 10/071,097

(22) Filed: Feb. 11, 2002

(65) Prior Publication Data

US 2003/0021463 A1    Jan. 30, 2003

(30) Foreign Application Priority Data

Jul. 25, 2001    (JP) .............................. 2001-224017

(51) Int. Cl.
    *G06K 9/00*    (2006.01)
(52) U.S. Cl. ...................... 382/145; 382/108; 382/199; 356/69; 250/559.36; 702/34; 348/128
(58) Field of Classification Search ........ 382/141–152, 382/108, 199, 291; 356/69, 237.2; 250/559.36; 702/34; 348/128
    See application file for complete search history.

(56) References Cited

U.S. PATENT DOCUMENTS 4,750,140 A * 6/1988 Asano et al. ............... 382/108
4,792,232 A * 12/1988 Jobe et al. .................. 356/394
5,805,728 A * 9/1998 Munesada et al. .......... 382/199
6,433,348 B1 * 8/2002 Abboud et al. ........ 250/492.22
6,781,688 B1 * 8/2004 Kren et al. ............... 356/237.4
6,839,470 B1 * 1/2005 Ikeda .......................... 382/266

FOREIGN PATENT DOCUMENTS

JP    2001-183116    7/2001
JP    2001-224017    8/2001

OTHER PUBLICATIONS

Japanese Laid-open No. 08-014836.
Japanese Laid-open No. 2000-058410.
1998 IEEE/SEMI Advanced Semiconductor Manufacturing Conference (P. 259-261).
J. Vac. Sci. Technol. B16(6), Nov./Dec. 1998 (P. 3739-3743).
IEEE Electron Device Letters, vol. 22, No. 6, Jun. 2001 (P. 287-289).

* cited by examiner

*Primary Examiner*—Jingge Wu
*Assistant Examiner*—Aaron Carter
(74) *Attorney, Agent, or Firm*—Antonelli, Terry, Stout and Kraus, LLP.

(57) ABSTRACT

The present invention provides a circuit pattern edge inspection method of finding out a failure in a fabricating process and image distortion in an observing apparatus by analyzing, by a non-destructive inspection, the shape of an edge of a line of a fine pattern in which characteristics of the material, process, and an exposure optical system in a semiconductor fabricating process appear, and performing analysis quantitatively. The method includes a step of detecting a set of edge points indicative of positions of edges of the pattern in a two-dimensional plane by a threshold method; a step of obtaining an approximation line for the set of edge points detected; and a step of obtaining an edge roughness shape and a characteristic by calculating the difference between the set of the edge points and the approximation line. A plurality of values are used as thresholds used for the threshold method.

6 Claims, 13 Drawing Sheets

METHOD AND APPARATUS FOR CIRCUIT PATTERN INSPECTION

BACKGROUND OF THE INVENTION

The present invention relates to a circuit pattern inspection technique and, more particularly, to a method and apparatus for observing a fine pattern by using a scanning microscope and inspecting an edge shape of the fine pattern.

In an LSI process, particularly, a microfabrication process performed after ArF lithography in recent years, as a pattern is becoming finer, the problem of roughness at the edge of a pattern is becoming bigger.

The occurrence of roughness is caused by the property of the material itself, exposure equipment, a substrate, or an observing apparatus itself. In a mass production process, the degree of roughness exerts a large influence on the performance of a product. Even when roughness is not abnormally large, appearance of characteristic roughness is often a reflection of deterioration in performance of a manufacturing apparatus, so that a failure may occur in a product in future. Consequently, development of a system for observing the shape of roughness at edges of a pattern and specifying the cause from the characteristic of the roughness is urgently necessary. Considering that the system is used in a mass production process, the inspection method has to be a non-destructive one.

Conventionally, information is empirically obtained mainly by view observation of an observed image by a scanning electron microscope. For example, there is a case that a state where right and left edges fluctuate synchronously can be seen at the time of observing a line pattern of a resist. In this case, the causes can be considered as follows for example: due to a narrow line, the top of a pattern fluctuates at the time of development, a light intensity distribution at the time of exposure fluctuates, and the observed image itself is distorted. There is also a case that roughness is seen relatively small around the surface but is seen large on the bottom portion of a pattern. From such a phenomenon, the possibility that the chemical property of the resist material does not match that of the substrate well and a residual is caused is considered.

However, such criteria of determination are not quantitative, the conclusion varies depending on observers. In order to systematically analyze the cause of occurrence of roughness without depending on the observer, the shape of roughness has to be quantitatively determined.

An example of the conventional attempt to quantitatively express the characteristic of the shape of the pattern edge is disclosed in the document, "B. Su, T. Pan, P. Li, J. Chinn, X. Shi, and M. Dusa, Proc. 1998 IEEE/SEMI Advanced Semiconductor Manufacturing Conference, p259 (1998)". According to the method, the taper shape of a line pattern edge is expressed by numbers from an SEM image. Although information of the edge portion in a cross sectional shape can be obtained to a certain degree, the characteristic of an edge in the direction along a line edge cannot obtained. A value obtained is an index of inclination of a side face of an edge, so that roughness cannot be evaluated.

A general method of detecting roughness of a pattern edge is a method of obtaining some deviations of edge positions from a straight line and calculating a standard deviation σ in a distribution of the deviations or a value which is three times as large as π. However, the roughness herein denotes accurately a dimensional error as used in the documents, "S. Mori, T. Morisawa, N. Matsuzawa, Y. Kamimoto, M. Endo, T. Matsuo, K. Kuhara, and M. Sasago, J. Vac. Sci. Technol. B16, p739 (1998)" and "C. H. Diaz, H. Tao, Y. Ku, A. Yen, and K. Young, IEEE Electron Device Letters 22, p287 (2001)" and is not an index used to evaluate the shape of an edge.

As described above, conventionally, there is no method of quantitatively evaluating the shape of an edge. Although the stereoscopic shape of an edge can be determined by view observation, it depends on the observer.

SUMMARY OF THE INVENTION

An object of the invention is to provide a method and apparatus for circuit pattern inspection capable of converting evaluation of the shape of an edge, which is conventionally performed by view observation of an image into numbers, evaluating the edge shape quantitatively and promptly with high precision, and specifying the cause of occurrence of roughness systematically.

In the invention, a data process is directly performed on a two-dimensional distribution image of secondary electrons or reflected electrons obtained by observation with a scanning microscope using a charged particle beam such as an electron beam, ionizing radiation, or an ion particle beam to obtain positions of edge points by a threshold method while keeping the precision of the microscope, and deviations of the edge point positions from an approximation line, that is, edge position fluctuations are computed. A set of the edge position fluctuations computed with respect to edge points belonging to one edge expresses a two-dimensional characteristic of the shape of edge roughness. The computing operation is performed by using different thresholds to obtain a plurality of sets of edge position fluctuations. By the sets, the shape of the three-dimensional edge roughness of the original image is shown.

There is also provided a step of calculating and displaying a spatial frequency distribution of the edge position fluctuations and the dependency on the threshold of the fluctuations. Consequently, a spacial period in which the intensity is particularly high, that is, the period showing the characteristic of the roughness can be found out.

By providing a step of calculating and displaying the dependency on the threshold of the standard deviation of edge position fluctuations, the case where the edge roughness is large around the surface and the case where the edge roughness is large in the bottom portion can be distinguished from each other. In the former case, it can be estimated that the cause of occurrence of roughness is an atmosphere during a patterning process. In the latter case, it can be estimated the cause is mismatch of the patterned material with an underlayer.

There is also provided a step of calculating a correlation of fluctuations in the right and left edge positions of one line, a coefficient of correlation, and dependency on the threshold of the coefficient of correlation, and drawing view graphs based on the calculation results. Consequently, whether the directions of roughness of the right and left line pattern edges are (1) the same direction (FIG. 1), (2) opposite to each other (FIG. 2), or (3) at random, and whether the types of the roughness changes in the depth direction or not can be made clear.

FIGS. 1 and 2 show examples of the types of the roughness of edges in the case where one line pattern exists in the vertical direction in an image. In the diagrams, reference numerals 1 and 3 denote left edges of the line, and 2 and 4 indicate right edges.

FIG. 1 shows a case where the width of the line is constant but the line itself is wavy. FIG. 2 shows a case where the right and left edges of the line are synchronous but fluctuate in the opposite directions different from FIG. 1. When there is the tendency of (1), the correlation between the fluctuations in the right and left edge positions is positive. When there is the tendency of (2), the correlation between the fluctuations in the right and left edge positions is negative. When the right and left edges fluctuate independently, there is no correlation. Concrete calculation and criteria of determination of the coefficient of correlation will be described herein later.

There are also provided a determining function, in which possible steps where roughness is considered to occur are selected based on the calculation results, and a function of displaying them. By using a system capable of transmitting a signal to a proper apparatus, a loss can be reduced by a conventional system in quick response to appearance of a failure.

When the possibility that the cause of the edge roughness is the observing apparatus itself is pointed out, to check the observing apparatus, a standard sample of the shape of a line is observed, an observation position is moved in a direction parallel to the line pattern while acquiring image data, and images are added up. Although roughness which occurs at random in the obtained two-dimensional data is averaged, distortion in an observed image remains without being eliminated. By storing the distortion amount as data, distortion is eliminated in observation later, so that an image having a smaller error can be obtained.

According to the invention, there is provided a circuit pattern inspection method of inspecting a pattern shape on the basis of two-dimensional distribution information of intensities of secondary electrons or reflected electrons obtained by observing a pattern formed on a substrate by a scanning microscope using a charged particle beam, characterized by including: a step of detecting a set of edge points indicative of positions of edges of the pattern in a two-dimensional plane from the two-dimensional distribution information by a threshold method; a step of obtaining an approximation line for the set of edge points belonging to the edges detected; and a step of obtaining an edge roughness shape by calculating the difference between the set of the edge points and the approximation line.

According to the invention, there is also provided a circuit pattern inspection method of inspecting a pattern shape on the basis of two-dimensional distribution information of intensities of secondary electrons or reflected electrons obtained by observing a pattern formed on a substrate by a scanning microscope using a charged particle beam, characterized by including: a step of detecting a set of edge points indicative of positions of line edges of the pattern in a two-dimensional plane from the two-dimensional distribution information; a step of obtaining an approximation line for the set of edge points detected for each line edge by least square; a step of obtaining an edge roughness shape by calculating the difference between the set of the edge points belonging to each line edge and the approximation line; and a step of displaying correlation between edge roughness shapes of different line edges.

The invention is characterized in that, in the above configuration, a plurality of values are used as thresholds used for the threshold method.

The invention is also characterized in that the above configuration further includes a step of calculating a spatial frequency distribution of the edge roughness shape obtained.

The invention is also characterized in that the above configuration further includes a step of obtaining the degree of the edge roughness by calculating a standard deviation expressed by the square root of an average of root-mean-square values of the differences each between the set of the edge points derived with respect to the plurality of thresholds and the approximation line.

The invention is also characterized in that the above configuration further includes a step of selecting a candidate of a process of forming a pattern of the substrate, which causes occurrence of roughness from the edge roughness shape obtained, and displaying the candidate.

Further, the invention provides a circuit pattern inspection method including: a step of mounting a sample processed in a line pattern shape at a predetermined pitch on a scanning microscope, observing the sample, and obtaining a two-dimensional intensity distribution of secondary electrons or reflected electrons; a step of calculating a shape of roughness of an edge of the line pattern from the two-dimensional intensity distribution; and a step of storing the edge roughness shape obtained as image distortion information of the scanning electron microscope.

Further, the invention provides a circuit pattern inspection method including: a step of mounting a sample processed in a line pattern shape at a predetermined pitch on a scanning microscope, observing the sample, and obtaining a first two-dimensional intensity distribution of secondary electrons or reflected electrons; a step of moving an observation position in the direction of an edge of the line pattern only by a predetermined length and obtaining a second two-dimensional intensity distribution of secondary electrons or reflected electrons; a step of computing a sum of the first and second two-dimensional intensity distributions; a step of calculating a shape of roughness of an edge of the line pattern from the sum data; and a step of storing the edge roughness shape obtained as image distortion information. Further, according to the invention, the above circuit pattern inspection method may further include a step of calculating an image offset amount in the direction perpendicular to an edge of a line pattern in an observation area from the image distortion information obtained and correcting a third two-dimensional intensity distribution of secondary electrons or reflected electrons obtained as a result of observing an arbitrary sample or a pattern edge position obtained from the third two-dimensional intensity distribution.

Further, the invention provides a circuit pattern inspection apparatus characterized by including: a charged particle source; a charged particle optical system for irradiating a sample with a charged particle beam emitted from the charged particle source through a condenser lens, a deflector, and an object lens, deflecting the beam, and performing the scan with the beam; a stage on which the sample is to be mounted; a detector for detecting intensity of a secondary electron or reflected electron emitted from the sample by irradiation of the charged particle beam; a control system for controlling the deflection and scanning; and signal processing means for obtaining an edge roughness shape and a characteristic of the pattern on the basis of a threshold method from a two-dimensional distribution of intensities of the secondary electrons or reflected electrons obtained.

DETAILED DESCRIPTION OF THE PREFERRED EMBODIMENTS

Embodiments of the invention will be described hereinbelow with reference to the drawings.

First Embodiment

Figure 3:
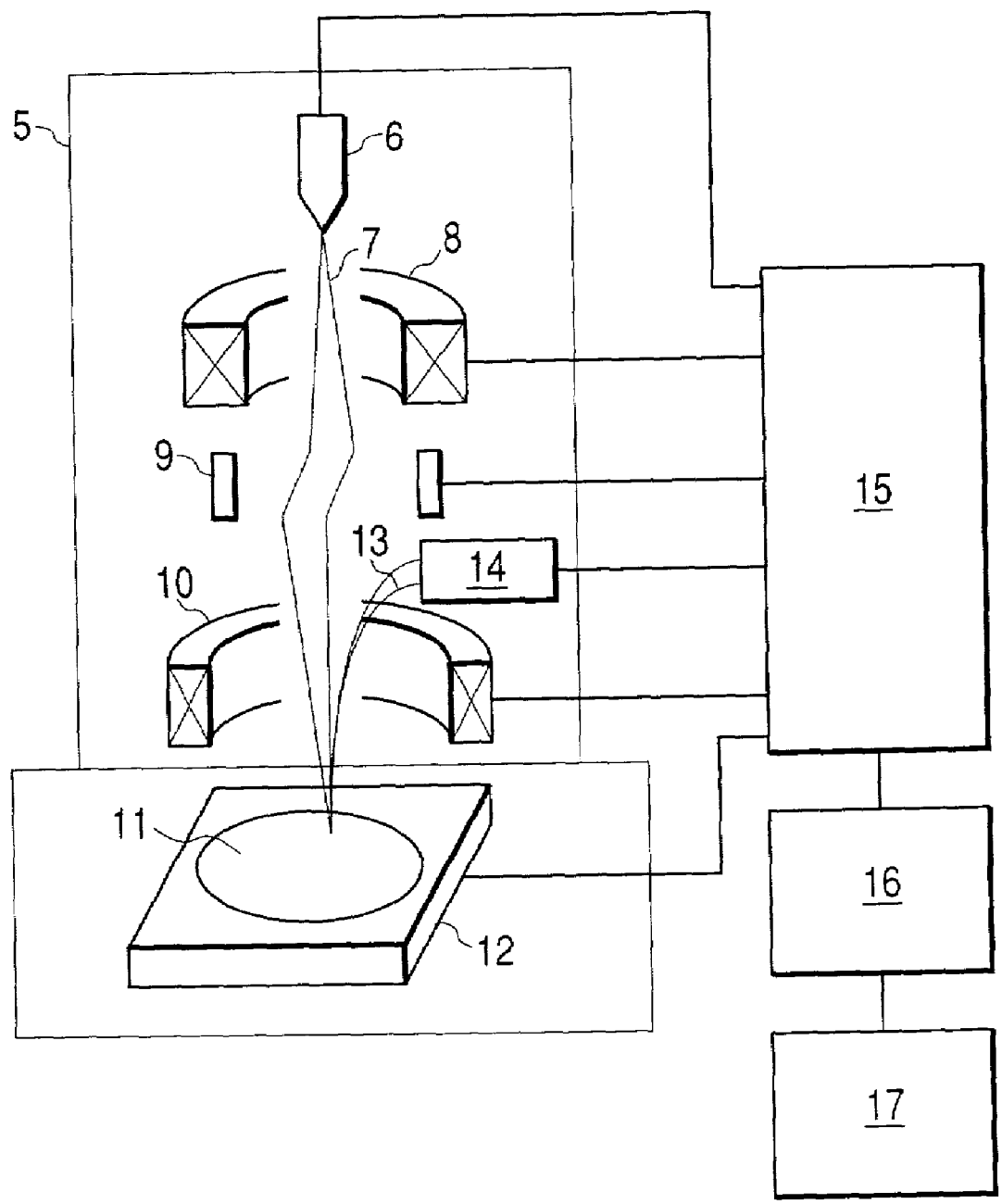
FIG. 3 is a conceptual diagram showing the configuration of an apparatus for carrying out the invention.
Figure 5:
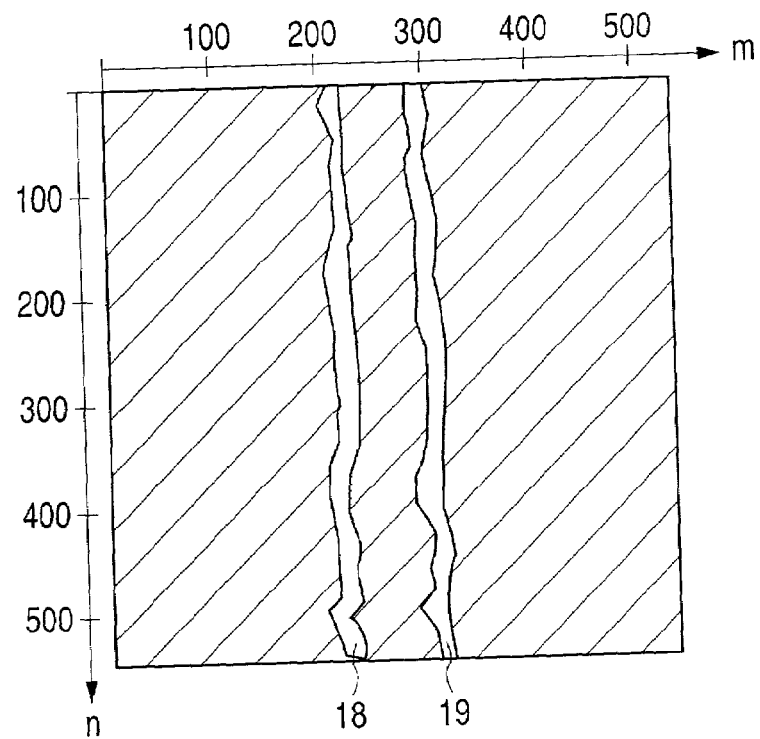
FIG. 5 is a schematic diagram of an observed image evaluated in the first embodiment of the invention.
Figure 6:
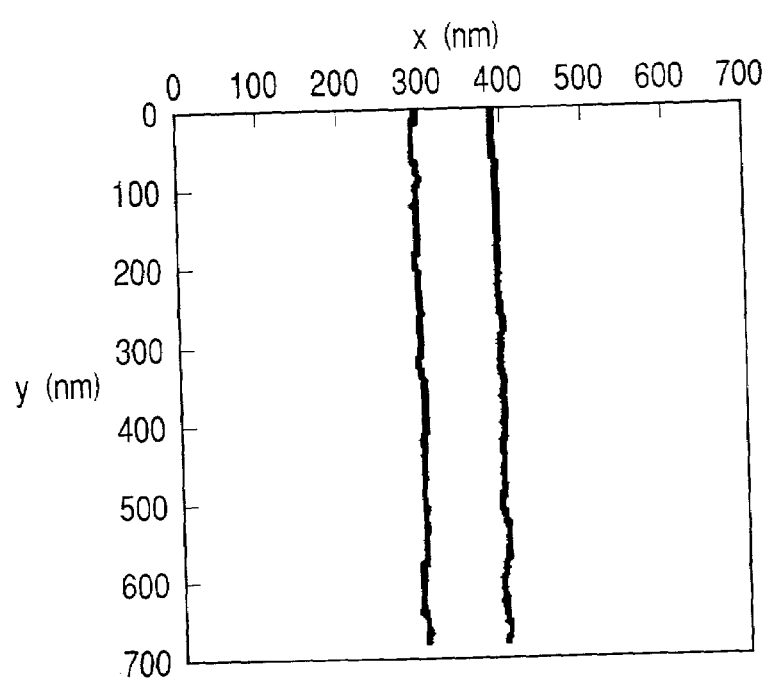
FIG. 6 is a diagram showing line edges obtained in the first embodiment of the invention.

A first embodiment of the invention will be described by referring to FIGS. 3 to 6. FIG. 3 is a schematic diagram showing the configuration of an apparatus of the embodiment, FIG. 4 is a flowchart showing the procedure of the embodiment, FIG. 5 is a schematic diagram showing an image formed from data used for evaluation, and FIG. 6 is a diagram showing edges of a line pattern detected with a threshold parameter of 0.5 from the data.

Figure 4:
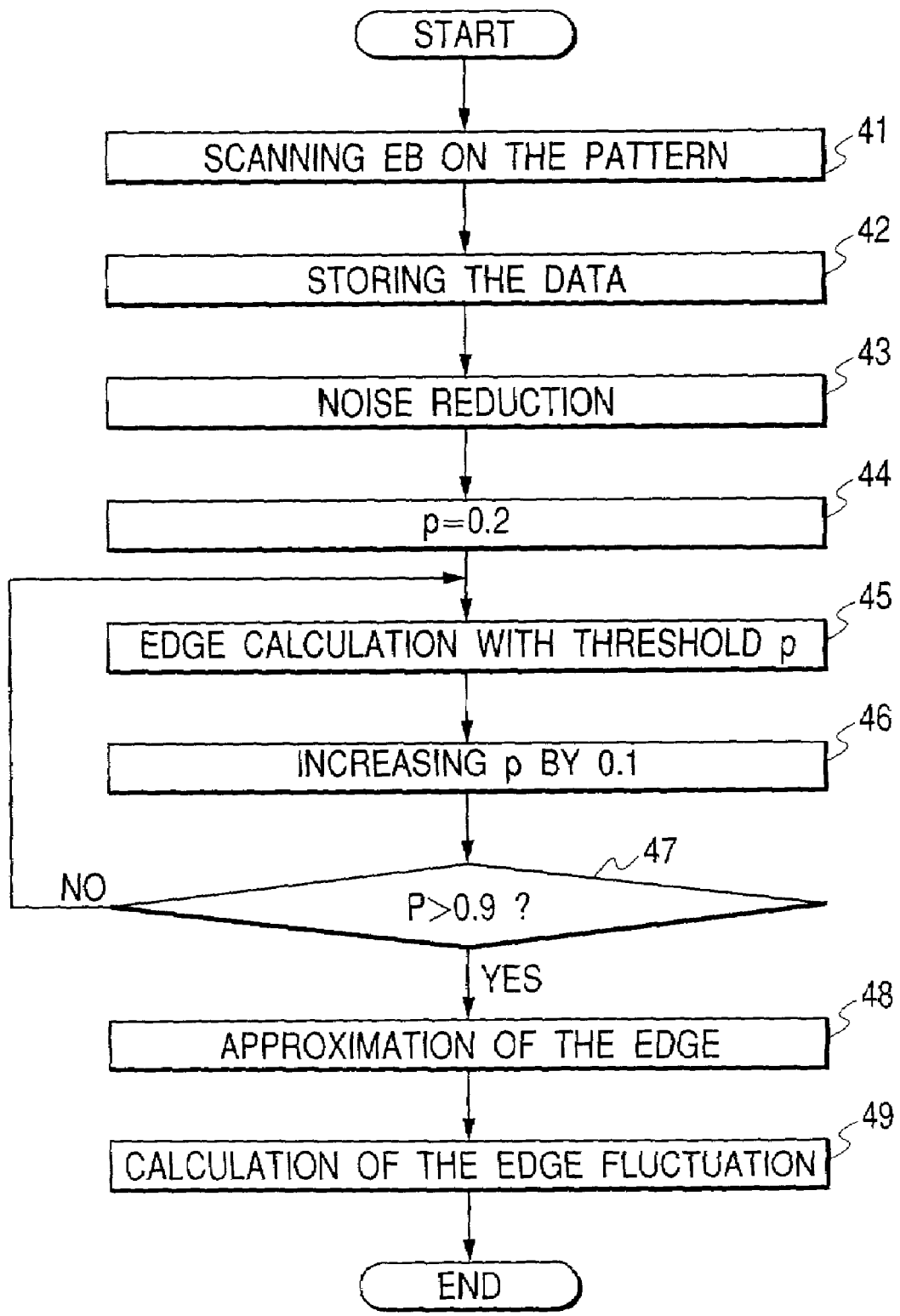
FIG. 4 is a flowchart showing the procedure of a first embodiment of the invention.

By using the apparatus shown in FIG. 3, an inspection is performed on a pattern in accordance with the flow shown in FIG. 4.

First, as shown in a step 41, by performing an operation from a control system 15 for a scanning electron microscope (SEM) a sample wafer 11 mounted on a stage 12 in a column 5 is observed. An electron beam 7 emitted from an electron emitter 6 of the SEM irradiates the sample wafer 11 on the stage 12 via a condenser lens 8, a deflector 9, and an object lens 10, and a secondary electron 13 emitted from the sample wafer 11 is detected by an electron detector 14.

The structure of the sample wafer 11 has a line pattern of a resist formed by electron beam drawing on a silicon wafer. In the case where there is no record of measurement with respect to a spatial period of edge roughness of the pattern or there is no particular request on the size of an observation area, it is desirable to observe a sample wafer at a magnification of 100,000 times to 300,000 times. In the example, the observation was made at a magnification of 200,000 times. The sample wafer 11 was mounted on the stage 12 so that the line pattern is almost perpendicular to the scan direction.

In step 42, scanning is performed a plurality of times, measurement results of the intensities of the secondary electrons emitted from the pattern are added up, and an average value is calculated. In order to obtain an image with a low level of noise, the desirable number of adding up of data is 64 times or more. In the example, the adding operation was carried out 128 times.

A distribution of two-dimensional electron intensities obtained in such a manner is data to be analyzed. The electron intensity distribution data obtained is converted to shades of a gray scale so as to be displayed as an image on the screen of a terminal of a computer 16 for analysis. FIG. 5 is a schematic diagram of the image.

The image data is composed of 512 pixels in the lateral direction and 512 pixels in the vertical direction. In the case of detecting the shape of edge roughness of an area which is long in the vertical direction, the pitch of scan lines corresponding to data in rows can be set to an integral multiple of the pitch of pixels in the lateral direction. For example, an area having a width of 675 nm and a length of 2700 nm can be displayed on a screen of 512×512 pixels. In this example, an observation area included in an image has a length of 675 nm and a width of 675 nm. One pixel corresponds to an area having about 1.318-square nm. Hereinbelow, the upper left of an image is set as the origin, a distance to the right is expressed as x, and a distance downward is expressed as y. Numbers of pixels in the x and y directions are expressed as m and n, respectively. In reality, an image having shades according to the intensities of secondary electrons appears. In FIG. 5, an area in which the intensity of a secondary electron is particularly high, that is, an area where an edge may exist is expressed as blank and an area having a low intensity of the secondary electron is hatched. The coordinates shown in FIG. 5 indicate the numbers of pixels of an image. The electron beam is stopped from being continuously emitted to the wafer, after that, the image data is transferred from the control system 15 to the neighboring computer 16. The step 42 is finished and the program advances to step 43 where a program for analyzing a shape according to the invention is executed.

The program performs averaging and smoothing operations on the data as described below to thereby reduce noise. First, the data is divided into a set of 512 intensities of secondary electrons arranged in a line, that is, profiles. Each profile shows dependency on x of the intensity of the secondary electron in the case where y is constant. The number of profiles is equal to the number of pixels in they direction, that is, 512 in total.

The data is subjected to noise reduction by the following procedure. First, an averaging parameter $k_1$ (natural number) and a smoothing parameter $k_2$ (odd number) are given.

When $k_1$ is an even number, $k_1'=k_1/2$. When $k_1$ is an odd number, $k_1'=(k_1-1)/2$ and $k_2'=(k_2-1)/2$. An average of $k_1$ profiles from the $(N-k_1')$ th profile is calculated and used as the n-th profile averaged. Smoothing operation using a Hamming window is performed on an area from pixel number $m-k_2'$ to pixel number $m+k_2'$ in the averaged profile obtained in the preceding step, thereby newly obtaining an m-th value smoothed. In the case of data in which one pixel corresponds to a length from 0.8 nm to 2 nm, desirably, the averaging parameter $k_1$ is in a range from 4 to 11, and the smoothing parameter $k_2$ is in a range from 3 to 11. If any of the parameters is below the corresponding range, noise cannot be sufficiently reduced. If it is over the range, edge roughness in a fine spatial period cannot be detected. In this example, $k_1=k_2=7$ was set.

Subsequently, to detect edges of a line, an area for retrieving edge points is input. First, with respect to the left edge, from the position of an area 18 in FIG. 5, the pixel numbers in the x direction of the retrieval area are determined by eye-estimation as m=210 to 250 and entered. Similarly, with respect to the right edge, the pixel numbers were determined from the position of an area 19 by eye-estimation as m=280 to 320. The calculation areas can be designated by two ways: (1) entry of numerical values, and (2) entry on the screen of FIG. 5. In this example, numerical values were entered.

Subsequently, as shown in steps 44 to 47, the edge points are detected. The threshold parameter p for detection is used while being changed from the smallest value $p_1$ to the largest value $p_2$ of the set values p at a set pitch of $\Delta p$. In the example, with respect to the values of $p_1=0.2$, $p_2=0.9$, and $\Delta p=0.1$, the operation was performed on total 256 profiles whose pixel numbers n in the y direction are even numbers 2n'. A threshold method used here is a generally known method in which, from the threshold parameter p and the highest value $I_{max}$ and the lowest value $I_{min}$ of the secondary electron intensity, the threshold obtained by $(I_{max}-I_{min}) \times p + I_{min}$ is calculated and points at which the intensity of the secondary electron becomes equal to the threshold on the profiles are used as edges.

X coordinates at the right and left edge points detected are set as $x_R(2n')$ and $x_L(2n')$, respectively. The profile is a set (x, I (x)) of numerical values I giving the secondary electron intensity at the position to the x coordinate expressed by an integral multiple of the length 1.318 nm of one pixel in the x direction. At the time of calculation, neighboring points are connected with straight lines, and the intersections between the polygonal line and the threshold value are obtained. The y coordinate of the edge point obtained in such a manner is 2n'×1.318 (unit: nm).

By the above process, for one value of p, 256 ($x_L$, y) coordinates can be derived with respect to the left edge. Similarly, a set of 256 points can be obtained with respect to the right edge. A process of setting 0.2 as the value of p (step 44), detecting an edge, and increasing the value p by 0.1 is repeated until the value p becomes 0.9 (steps 45 to 47). As an example, FIG. 6 shows a set of edge points obtained in the case where p=0.5.

As shown in step 48, total 512 points of the right and left edges are approximated by using least square. Generally, it is possible to approximate the edge points with arbitrary functions. In this case, we use a set of parallel straight lines x=ay+b and x=ay+b+w.

In step 49, with respect to a profile obtained when the y coordinate is an even number 2n', the difference between the x coordinate $x_L(2n')$ at the left edge point and the intersection of the approximate straight line and the profile, that is, the x coordinate a×2n'+b at the approximate point is calculated as an edge point fluctuation $\Delta x_L(2n')$. The calculation is similarly performed with respect to the profiles from n'=1 to n'=256, thereby obtaining fluctuations at the 256 left edge points. At the time of calculation, the positions of the points are expressed by x and y in the unit of length of nm. However, the process may be performed by expressing the positions of the points by pixel numbers m and n. In the latter case, n is a positive integer, so that a storage capacity to be used can be small. Similar calculation is also executed with respect to the right edges, thereby obtaining 256 right edge point fluctuations. In such a manner, the set of edge position fluctuations $(\Delta x_L(2n'), 2n')$ $(\Delta x_R(2n'), 2n')$ (where, n'=1, 2, . . . , and 256) indicative of the shape of edge roughness can be obtained. The program also calculates the values for every threshold. The results of the calculations are stored in the storage area in a computer.

As a result, the shape of edge roughness can be taken out as digital data from a microphotograph expressed in shades of the gray scale and can be displayed as a set of points on a graph. Consequently, the edge shape can be display more clearly. An analysis is further conducted by using the data, so that the pattern shape can be analyzed as well.

Second Embodiment

A second embodiment of the invention will be described by referring to FIGS. 5 and 7.

By the method described in the first embodiment, edge positions are detected from the image data of a resist pattern shown in FIG. 5 and, further, data indicative of an edge roughness shape is obtained as fluctuations in the edge positions.

Subsequently, a set of edge position fluctuation data $(\Delta x_L(2n'), 2n')$ (or a set of $(\Delta x_R(2n'), 2n')$) obtained at each threshold is regarded as a summation of periodical functions in the y direction and a distribution of the periods is obtained. Specifically, Fourier transform is performed on a data series $\{\Delta x_L(2), \Delta x_L(4), \Delta x_L(6), \Delta x_L(8), \ldots\}$ to obtain the absolute value of a Fourier coefficient for a spatial frequency (f) in the y direction, that is, the intensity A(f).

Figure 7:
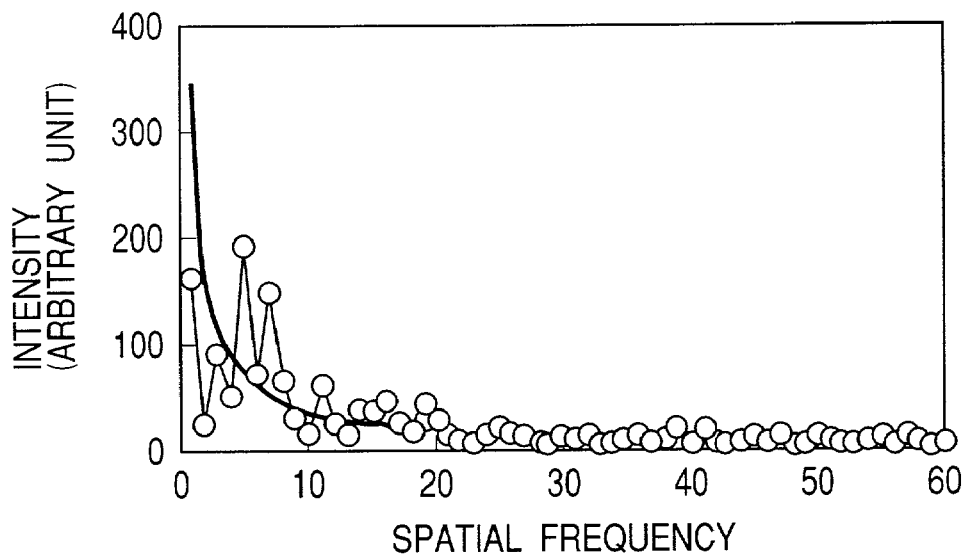
FIG. 7 is a diagram showing a spatial frequency distribution of line edge roughness obtained in a second embodiment of the invention.

FIG. 7 shows an example of the frequency distribution derived as a result. This is the result of the Fourier transform performed on the left edge of the line illustrated in FIG. 6. The spatial frequency (f) on the lateral axis denotes a ratio of the image area length 675 nm to the corresponding spatial period. For example, f=10 corresponds to a space period of 675 nm/10, that is, 67.5 nm.

Next, the characteristic spatial frequency in the frequency distribution is extracted by the following procedure. The intensity A(f) in the area of 15<f<128 is approximated by a function $A_0 \times 1/f$ by using least square, and the function $A_0 \times 1/f$ for which a fitting parameter $A_0$ obtained is substituted is plotted onto the graph in all of areas where f<128. The curve expressed by a thick solid line in FIG. 7 is an approximated curve derived in such a manner. A(f) as an actually measured value in a preliminarily designated area of (f) is compared with the approximation value $A_0 \times 1/f$. The value (f) at which A(f) is larger than $A_0 \times 1/f$ is picked up. In the example, the designated area was set as 3<f<20.

The analysis was performed on the right and left edge roughness at all the threshold parameters. From the analysis, it was found that the components of the spatial frequency of f=5 and f=7 largely contribute to the roughness.

As one of quantities characterizing the edge roughness obtained in such a manner, the space period which can be said as characteristic roughness can be extracted. As described above, as a result of inspecting the pattern shown in FIG. 5, numerical values f=5 and f=7 were obtained. When the roughness at the constant frequencies are observed irrespective of the thresholds, considered are a case where a pattern is formed distorted over a full range from the bottom to the surface area and a case where the frequency components are distortion of an observed image. In the former case, the cause of the edge roughness is resist exposure equipment. In the latter case, the cause is the observing apparatus. As described above, by making the inspection, candidates of processes as the cause of occurrence of roughness can be selected.

Third Embodiment

A third embodiment of the invention will be described by referring to FIGS. 5, 8, and 9.

By the method described in the first embodiment, edge positions are detected from image data of a resist pattern shown in FIG. 5 and, further, data indicative of the shape of edge roughness is obtained as fluctuations in the edge positions.

Next, from the edge position fluctuation data obtained at the thresholds, an amount expressed by the following Equation 1, that is, a standard deviation in a fluctuation distribution is calculated, and a value 3σ which is three times as large as the standard deviation is defined as the degree of edge roughness.

$$\sigma = \sqrt{\frac{\sum_{n'} \Delta x_k(2n')}{256}} \qquad \text{(Equation 1)}$$

where an index k is equal to L or R. This calculation is executed at each threshold, thereby obtaining the relation between the threshold parameter p and the degree of roughness 3σ with respect to one line edge. FIG. 8 shows the result of the calculation executed on the example illustrated in the schematic diagram of FIG. 5. It is understood that the degree of roughness hardly depends on the threshold but is almost constant.

The graph of the dependency on the threshold parameter p of the degree 3σ of roughness can be also quantitatively analyzed as follows. The graph of the threshold parameter to 3σ is approximated by least square with a linear function y=ax+b where y is the value of 3σ (unit: nm) and x is the threshold parameter. The value of the obtained fitting parameter (a) is compared with a preset value $\alpha_1$. When a>$\alpha_1$, it is determined that 3σ increases as p increases, in other words, roughness is large around the surface. The value a is also compared with a preset value $\alpha_2$. When a<$\alpha_2$, it is determined that 3σ decreases as p increases, in other words, roughness is large around the bottom of the resist pattern.

From the results of inspections on line patterns of conventional resists, 4 and −4 are standard values as set values of $\alpha_1$ and $\alpha_2$, respectively. The observer can set other values.

Figure 8:
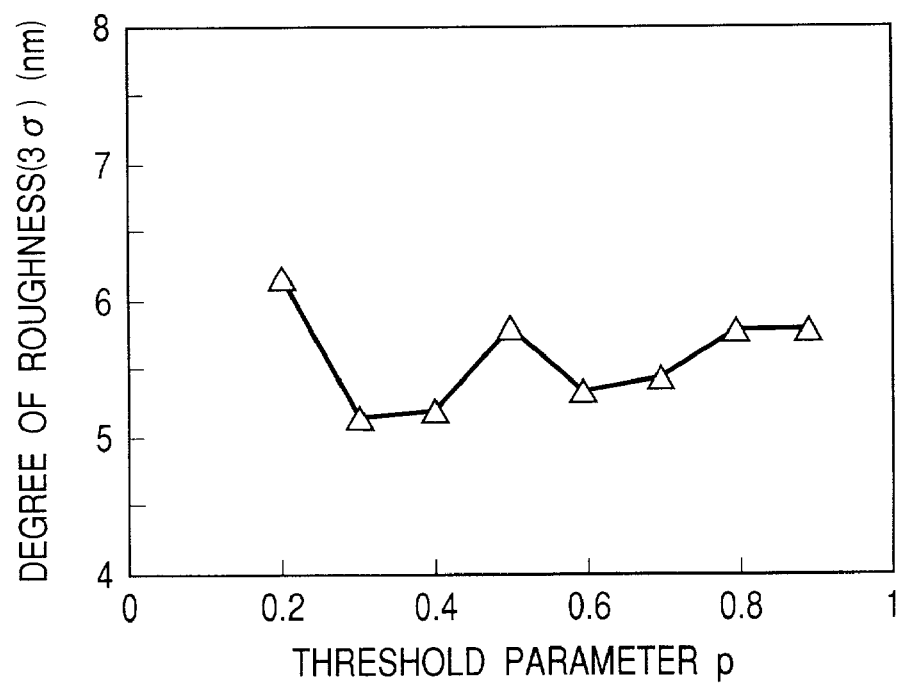
FIG. 8 is a diagram showing dependency (1) on a threshold of the degree of roughness of a line edge obtained in a third embodiment of the invention.

When the method is applied to the result illustrated in FIG. 8, (a) is equal to 0.02. It is therefore understood that the degree of the roughness is almost constant from the bottom of a pattern to a portion around the surface.

Figure 9:
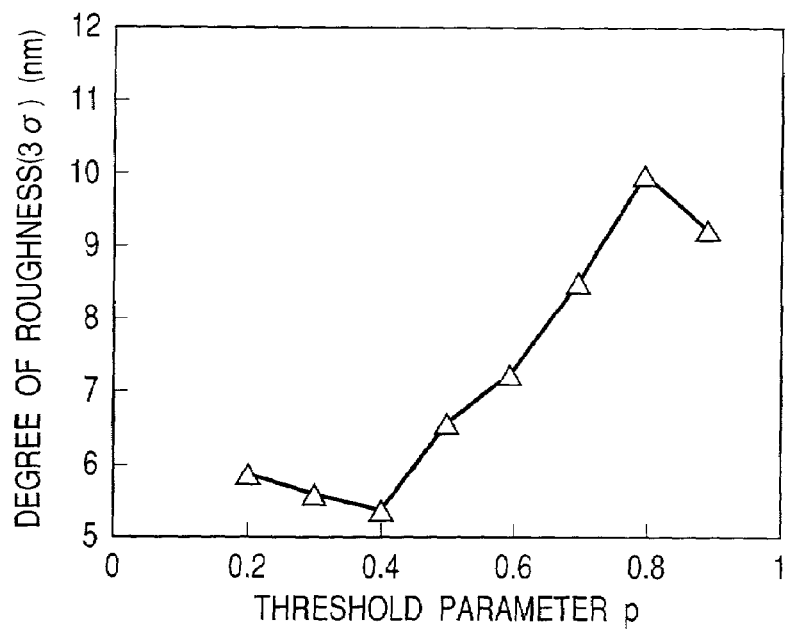
FIG. 9 is a diagram showing dependency (2) on a threshold of the degree of roughness of a line edge obtained in the third embodiment of the invention.

An inspection was also conducted on an image obtained by observing the pattern of another resist, and dependency on the threshold as shown in FIG. 9 was obtained. In this graph, the value (a) is 6.62 and it is determined that the roughness is large around the surface. Since the resist is a chemically amplified negative resist, it is pointed out that acids on the surface of the resist are possibly deactivated in an alkali atmosphere. The concentration of amine in the atmosphere was measured and it was confirmed that the concentration of amine was higher than before. In such a manner, from the dependency on the threshold of the degree of roughness, the candidate of the process causing roughness can be selected.

Fourth Embodiment

A fourth example of the invention will be described by referring to FIG. 5 and FIGS. 10 to 12.

By the method described in the first embodiment, edge positions are detected from image data of the resist pattern shown in FIG. 5 and, further, data indicative of an edge roughness shape is obtained as fluctuations in the edge positions.

Figure 10:
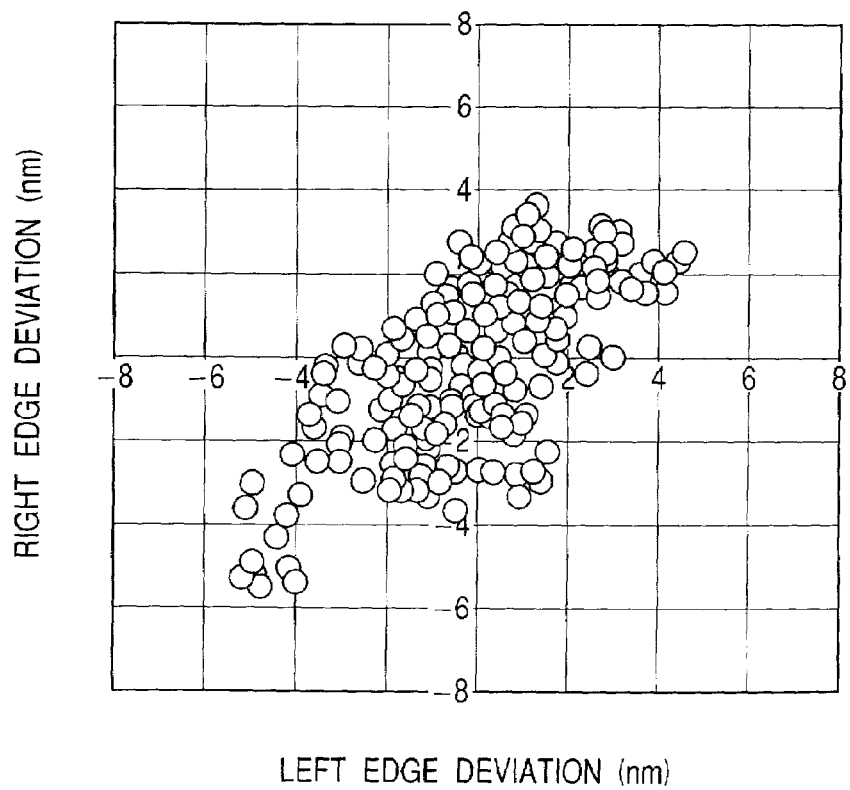
FIG. 10 is a diagram showing correlation between right edge roughness and left edge roughness in one line obtained by a fourth embodiment of the invention.

From a set of edge position fluctuation data ($\Delta x_L(2n')$, 2n') and a set of ($\Delta x_R(2n')$, 2n') obtained at each threshold, the fluctuations in the position of the left edge and those in the position of the right edge having the same y coordinate are combined, thereby obtaining 256 points (($\Delta x_L(2n')$, $\Delta x_R(2n')$). A graph is made from the points as shown in FIG. 10. This is the case where p=0.5.

From the result, it is understood that roughness of the right and left edges has a positive correlation. Based on the data, a coefficient ρ of correlation of the right and left edge position fluctuations when p=0.5 is calculated according to Equation 2. The numerator of the right side of Equation 2 is the amount expressed by Equation 3.

$$\rho = \frac{Cov(L, R)}{\sigma_L \cdot \sigma_R} \qquad \text{(Equation 2)}$$

$$Cov(L, R) = \frac{1}{256} \sum_{n'=1}^{256} \{\Delta x_L(2n') \cdot \Delta x_R(2n')\} \qquad \text{(Equation 3)}$$

$\sigma_L$ and $\sigma_R$ are standard deviations in the distributions of fluctuations of the left edge position and right edge position, respectively, and each of which corresponds to ⅓ of the degree of roughness. ρ is calculated as 0.64.

Figure 1:
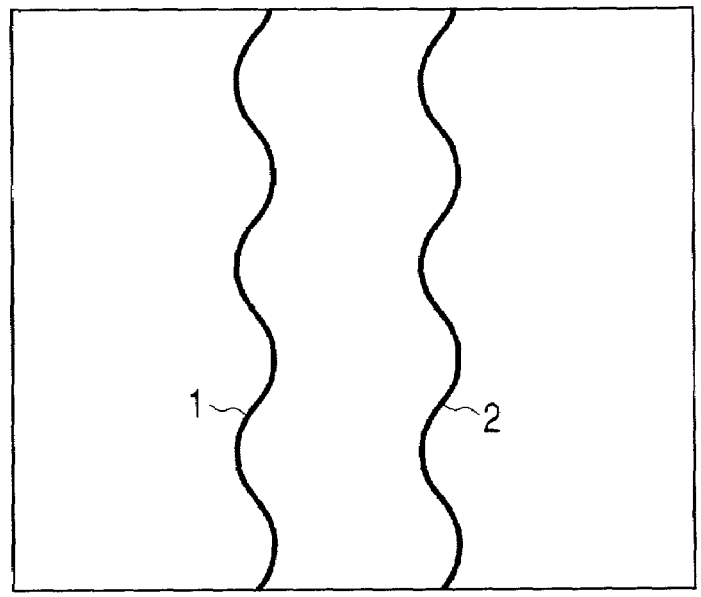
FIG. 1 is a schematic diagram of edges for explaining the first type of line edge roughness.
Figure 2:
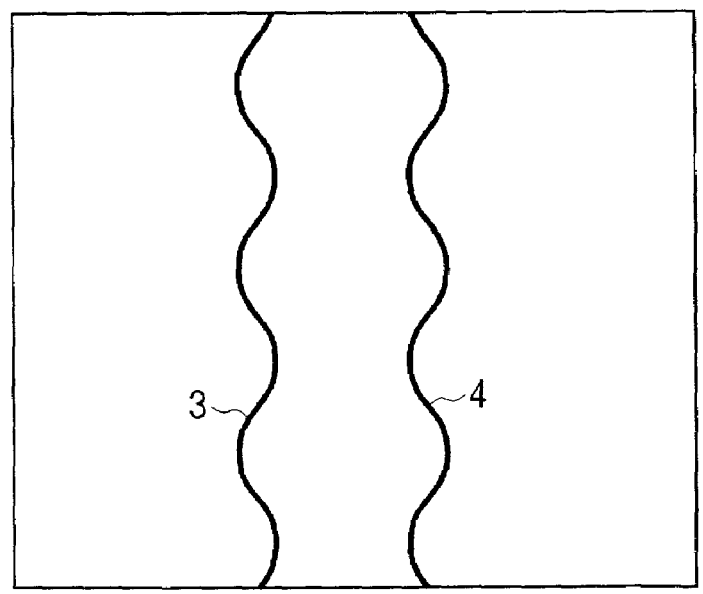
FIG. 2 is a schematic diagram of edges for explaining the second type of line edge roughness.

From the value ρ, the type of roughness can be classified as follows. The value ρ is compared with a preset reference value $\rho_{th}$ of the absolute value of ρ, and if ρ>$\rho_{th}$, the type of FIG. 1 is determined. If ρ<−$\rho_{th}$, the type of FIG. 2 is determined. If none of the cases, it is determined that there is no correlation. In the example, $p_{th}$ is set as 0.4. Although the value is a standard value, the observer can use another value. It is understood that the line pattern illustrated in FIG. 5 has roughness of the type of FIG. 1 when p=0.5.

Figure 11:
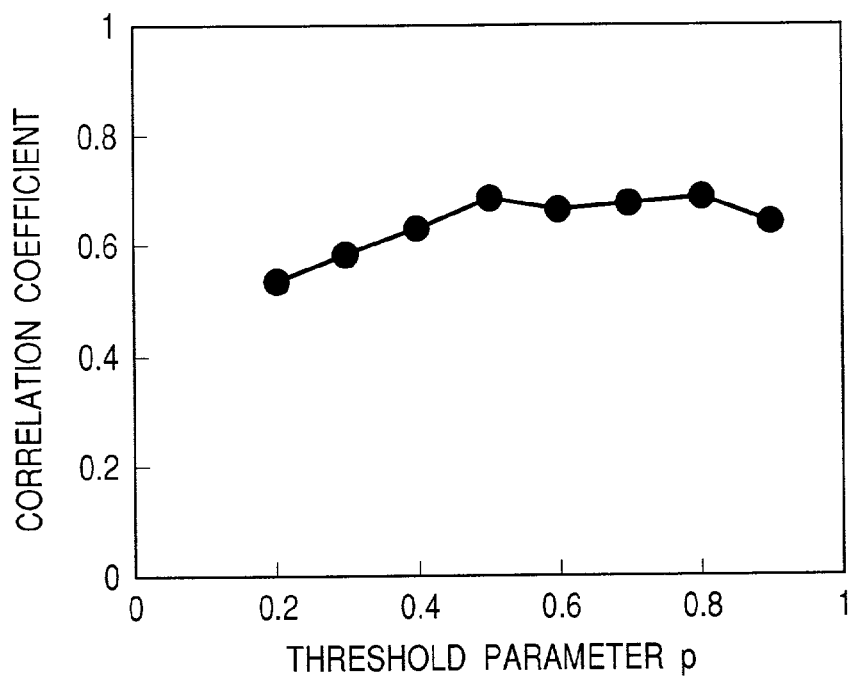
FIG. 11 is a diagram showing dependency (1) on the threshold of a correlation coefficient of right and left edge roughness in one line obtained by the fourth embodiment of the invention.

With respect to the line pattern illustrated in FIG. 5, further, while changing the value p from 0.2 to 0.9 at intervals of 0.1, the value of ρ was calculated. The result is shown in FIG. 11. It is found that dependency of ρ on p is small.

The graph of dependency of ρ on p can be also analyzed quantitatively as follows. The graph of the threshold p with respect to ρ is approximated with the linear function of y cx+d by least square. In this case, y is the value ρ, and x is the threshold p.

The value of the obtained fitting parameter c is compared with a preset value $\gamma_1$. When c>$\gamma_1$, ρ increases as p increases. That is, it is determined that the correlation between the right and left edge fluctuations is higher around the surface. When the value c is compared with a preset value $\gamma_2$, if $c<\gamma_2$, $\rho$ decreases as p increases. That is, it is determined that correlation between the right and left edge fluctuations is larger around the bottom of the resist pattern.

From the result of the inspections on the line pattern of the resist, conventionally, as the set values $\gamma_1$, and $\gamma_2$, 0.4 and −0.4 are standard values, respectively. Although the observer can set other values, in the example, the inspection was conducted by using the standard values.

When the method is applied to the result shown in FIG. 11, c becomes equal to 0.15, and it is understood that the correlation of the right and left edge fluctuations is constant from the bottom to the top of the pattern.

Figure 12:
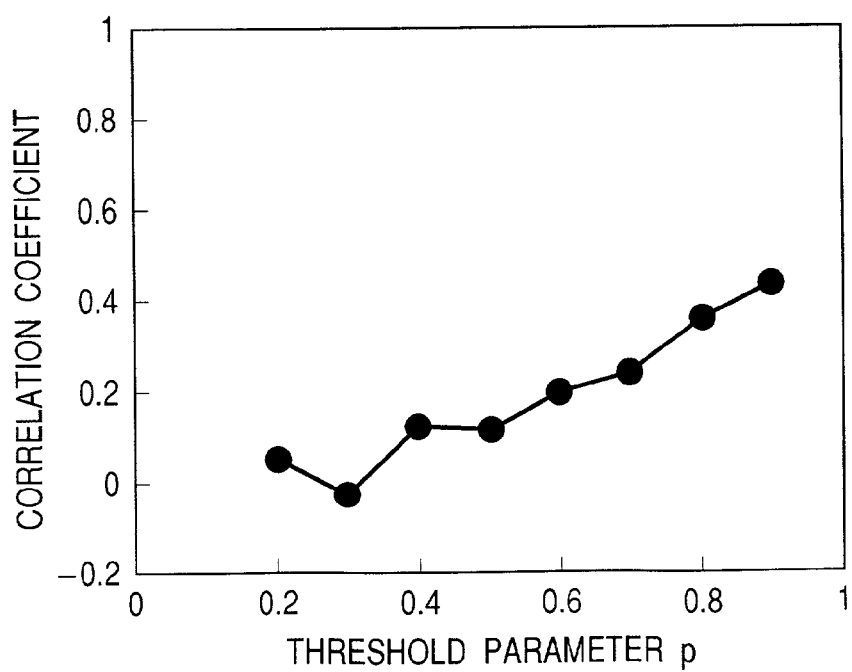
FIG. 12 is a diagram showing dependency (2) on the threshold of a correlation coefficient of the right and left edge roughness in one line obtained by the fourth embodiment of the invention.

An inspection was also conducted on an image obtained by observing the pattern of another resist, and dependency on the threshold shown in FIG. 12 was derived. In the graph, the value c is 0.57 and it is understood that the tendency that the right and left edges fluctuate together becomes stronger as the distance to the surface becomes shorter. Since there is no correlation of fluctuations of the right and left edges in the bottom part and the right and left edges fluctuate with the width being kept constant around the surface, it is estimated that a pattern once formed is distorted in the time of development or baking after the development due to its insufficient physical strength. As described above, from the dependency on the threshold of $\rho$, candidates of a process causing the roughness can be selected.

Fifth Embodiment

A fifth example of the invention will be described by referring to FIGS. 1 to 3, FIGS. 5 to 8, FIGS. 10, 11, 13, and 14.

Figure 13:
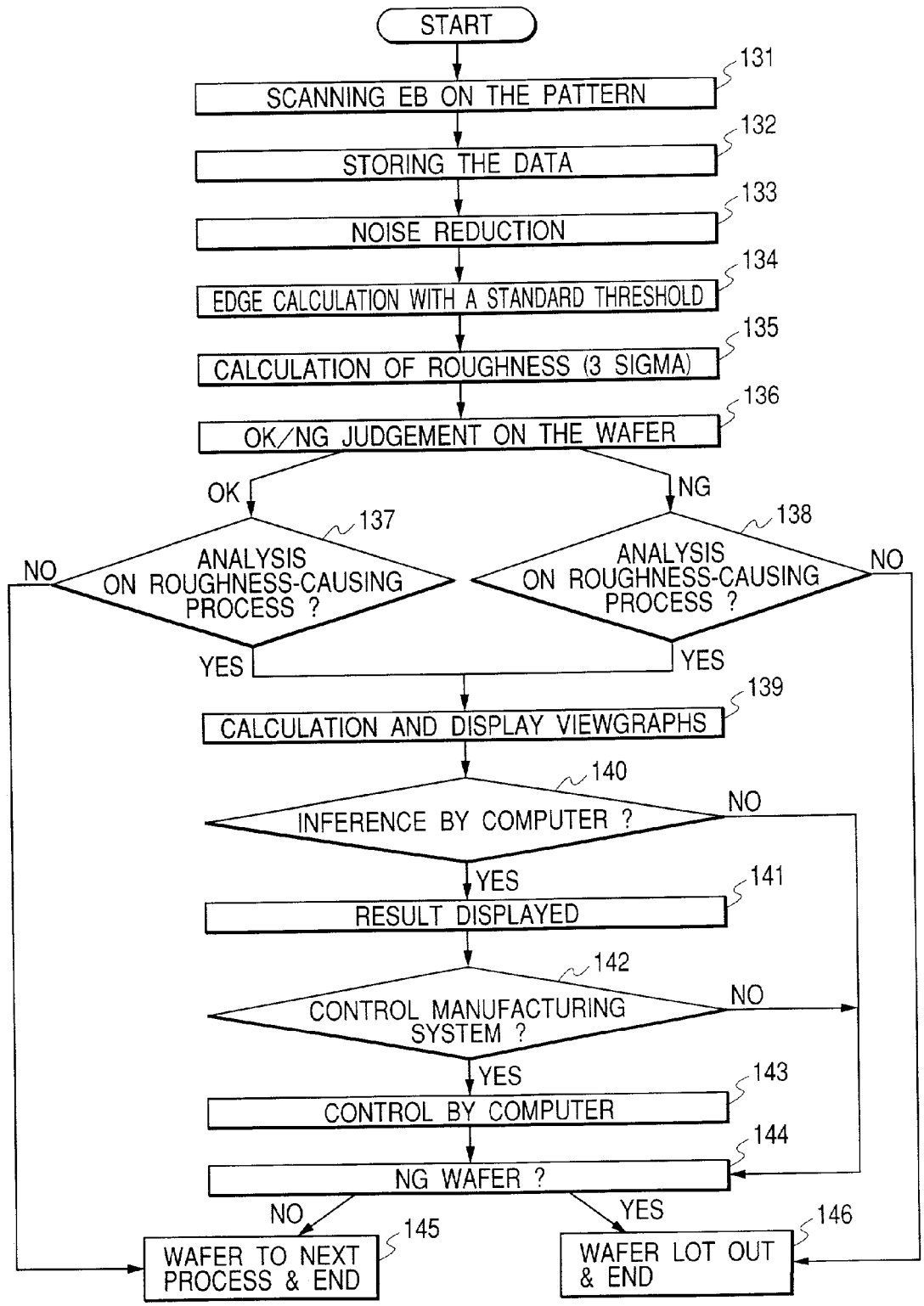
FIG. 13 is a flowchart for explaining the procedure of a fifth embodiment of the invention.
Figure 14:
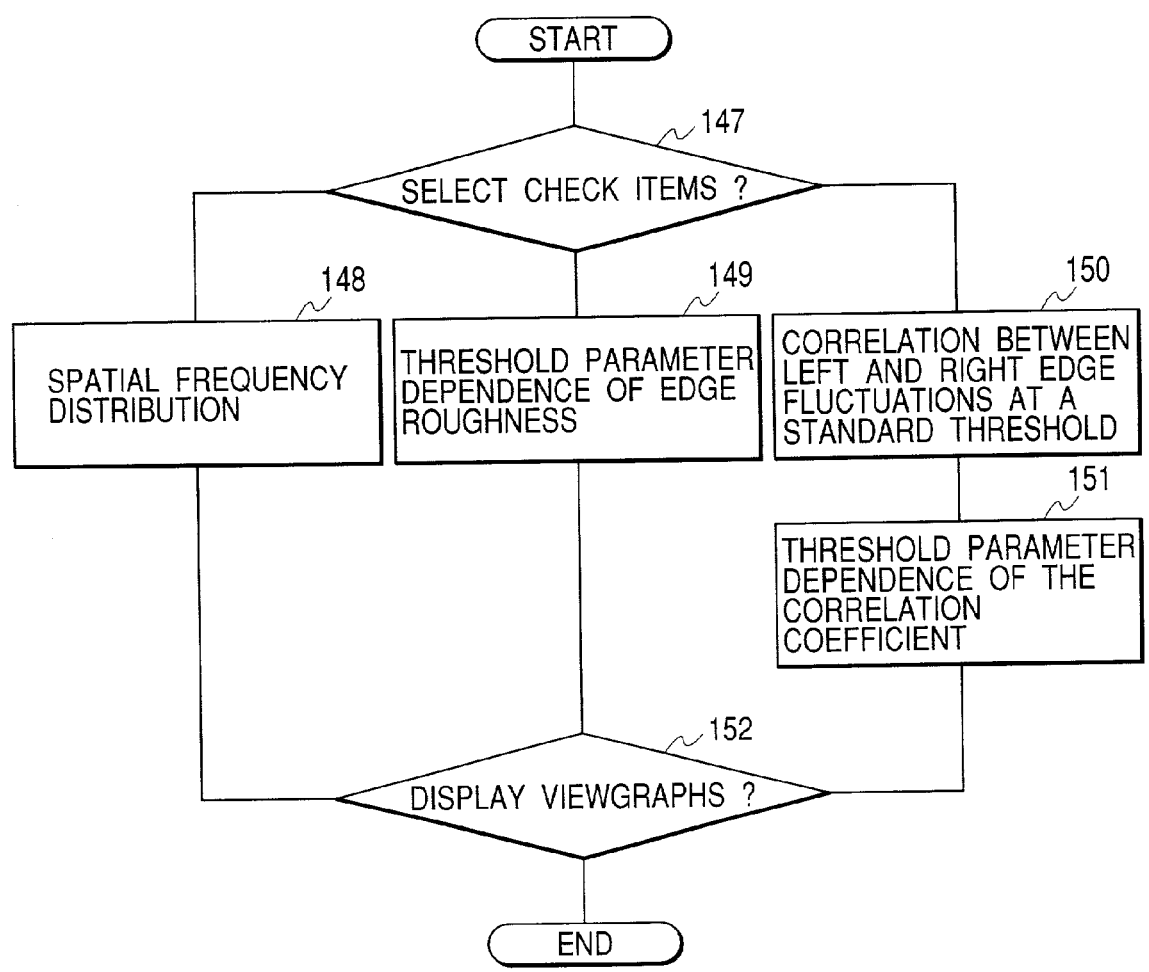
FIG. 14 is a flowchart for explaining a roughness analysis process in the flow shown in FIG. 13.

First of all, the outline of the procedure will be described with reference to FIGS. 13 and 14. FIG. 14 shows the details of a part of step 139 in the flow of FIG. 13.

By a procedure similar to that of the first embodiment, first, a line pattern is observed with a scanning microscope and data is captured (steps 131 and 132). Acquired two-dimensional data is subjected to noise reduction by the method described in the first embodiment (step 133), and the shape of edge roughness is obtained by using a standard value p (usually, 0.5) (step 134). Further, from the data of the edge roughness shape, with respect to all the edges in the image data, the degree ($3\sigma$) of roughness given by Equation 1 is calculated (step 135).

The program advances to step 136 and whether a wafer is good or not is determined. Only in the case where $3\sigma$ of all of the edges measured is smaller than a reference value, a wafer with a pattern to be observed is determined as good and passed to the following process. It is also possible to select whether the shape analysis in step 139 and subsequent steps is performed or not irrespective of the result of the determination (steps 137 and 138). If NO, the inspection on the wafer to be observed is finished. A good wafer is passed to the next step and a non-conforming wafer is taken out from the lot.

In the case of making the shape analysis, the program advances to step 139 where a line to be observed is selected from two-dimensional data of which noise has been reduced, and edge detection is sequentially performed by using a plurality of thresholds as described in the first embodiment to obtain data of an edge roughness shape with respect to each of the thresholds.

After the data is obtained, the data is processed according to the flow shown in FIG. 14. The data process includes three kinds of inspections for showing the characteristic of the edge shape and any of the inspections desired is selected (step 147). Although it is desirable to select all of the processes to obtain a result with high reliability, two or even one of the processes may be executed to shorten the execution time. The details of steps 148 to 150 will be described hereinbelow.

The first process is calculation of the space frequency showing the characteristic of the edge roughness shape. The spatial frequency distribution is calculated by a method described in the second embodiment and, after that, characteristic spatial frequencies common to the spatial frequency distribution of the edge roughness shapes at all the thresholds are picked up (step 148).

The second process is calculation of the dependency on the threshold of the degree of roughness. The dependency is calculated by the method described in the third embodiment (step 149).

The third process is calculation of a graph indicative of the correlation between right and left edge fluctuations belonging to one line with respect to thresholds, and calculation of dependency on the threshold of the correlation coefficient of the right and left edge fluctuations. They are calculated by the method described in the fourth embodiment (steps 150 and 151).

Analysis results of the items are displayed (step 152). After that, as shown in step 140 in FIG. 13, whether the roughness causing process is specified automatically or not is selected. In the case of No, if necessary, the above result is examined by the observer and the inspection on the wafer to be observed is finished. The wafer is processed according to the result of the determination of conformity (step 144). In the case of automatically specifying the roughness causing process, by checking the result with the reference in step 141, the program determines whether or not there is the possibility that any of the pattern generating processes causes the roughness and outputs the result. Further, in the case where the control on the fabricating apparatus in the pattern generating process is performed by the inspection apparatus, as shown in steps 142 and 143, a signal is sent to the fabricating apparatus in accordance with the result, the inspection on the wafer to be observed is finished, and the wafer is processed according to the determination of conformity (steps 144 to 146). The inspection performed in the example will be concretely described hereinbelow.

In the example, in a manner similar to the first embodiment, an image of a line pattern of an electron beam resist shown in the schematic view of FIG. 5 is inspected by using the apparatus shown in FIG. 3. The resist used for generating the pattern is a negative type.

First, two-dimensional data indicative of an image is processed by using the method and parameters described in the first embodiment, and edge roughness shapes of the right and left edges at the threshold p=0.5 are obtained. The shapes are as shown in FIG. 6. Subsequently, the degree of the right and left edge roughness is calculated by using the data and displayed together with the image. The sample to be observed is subjected to the determination of conformity and determined as a good item. The reference value of the roughness of the conforming item in the inspection is set to 6 nm. In the case where the sample is determined as a defective, an alarm sound is generated and the numerical values of roughness larger than the reference value are displayed in red in an image. The numerical values equal to or smaller than the reference value are displayed in white or black.

Although the sample was determined as good, the analysis on the shape of roughness was subsequently performed. First, by using the method and parameters described in the second embodiment, the spatial frequency was analyzed, the spatial frequency distribution at the threshold p=0.2 to 0.9 was obtained and, as characteristic frequencies common to the distributions, f=5 and 7 were found out. FIG. 7 shows the case where p=0.5.

By using the method and parameters described in the third embodiment, the dependency on the threshold p of the degree 3σ of roughness was calculated. A graph shown in FIG. 8 was displayed and a result such that the degree 3σ of roughness hardly depends on p was obtained.

Subsequently, by using the method and parameters described in the fourth embodiment, the correlation of the right and left edge roughness shapes was calculated as a coefficient of correlation, and the dependency on the threshold p of the coefficient of correlation was calculated. As a result, graphs shown in FIGS. 10 and 11 were obtained and it was found that the coefficient of correlation is positive and larger than the reference value, that is, the fluctuations are of the type shown in FIG. 1, and the tendency does not depend on the threshold The observer displayed the results and operated the automatic determining function of determining the roughness causing process. The procedure of narrowing candidates of the roughness causing process of a resist of a general automatic determining program will be described hereinbelow. For setting of values such as $\alpha_1$ and $\alpha_2$ used for the determining methods, setting of a reference used to narrow the candidates, and setting of exceptions, not only the general reference values used in the example but also data accumulated by the user are helpful. With them, roughness of a pattern of something other than the resist can be also inspected. In the example, a memory device is provided for the computer in order to accumulate data.

First, as candidates of the cause of roughness, (1) chemical property of the resist, (2) exposure equipment, (3) developer, (4) atmosphere, (5) the surface of the substrate, (6) underlayer pattern, and (7) observing apparatus can be mentioned.

Concretely, (2) indicates edge roughness of a reticle pattern or a position or strong fluctuation of a beam at the time of drawing. (3) indicates distortion of a whole line due to swelling caused by mismatch of the density of a developer or an eddy of the developer. (4) indicates erosion of the surface of a pattern by amine or acids in the atmosphere. (5) indicates footing due to the chemical nature such as insufficient processing on the surface of the substrate. (6) indicates unevenness of reflectance due to a lower layer pattern. (7) indicates distortion of an image due to electric noise or vibration.

Among the inspection items, in the calculation of the first frequency distribution, if p=0.5 and a characteristic frequency is not seen, there is the possibility that (1), (2), (4), and (5) out of the above causes are the causes, so that (3), (6) and (7) are eliminated. If a characteristic frequency is seen, the possibility of (5) is eliminated. If the frequency is 20 or higher, (7) is eliminated. When the characteristic frequency is converted to a period which is 0.5 μm or less, (3) is eliminated. When no characteristic frequency is seen at p=0.2 and 0.3 but is seen at p=0.8 and 0.9, (3) is possible. More specifically, it is considered that the physical strength of a resist is weak and an area around the surface is distorted by an external force generated after the pattern is formed, such as an eddy of the developer.

From the dependency on the threshold of the degree of roughness as the second inspection item, the following is determined. When it is determined that roughness is larger around the surface from the graph indicating the degree of edge roughness at p=0.2 to 0.9 by using the method described in the third embodiment, the causes (1) and (4) are possible but the others are eliminated. On the other hand, when it is determined that roughness is larger around the bottom of the pattern, there are possibility of (1) and (5).

As the third inspection item, when there is the correlation of right and left edge roughness at p=0.5 and the type shown in FIG. 1 is determined, there are the possibilities of (2), (3), and (7). In the case where the type shown in FIG. 2 is determined, there are the possibilities of (2) and (6). When the dependency on the threshold of the coefficient of correlation is calculated and, as a result, the correlation is large only around the surface, in addition to the roughness of the type of FIG. 1 or 2, the cause (5) is possible. Consequently, it is considered that roughness having no correlation between right and left edge roughness occurs around the bottom portion, so that roughness having large correlation between the right and left edge roughness (of the type of FIG. 1 or 2) is inconspicuous in the bottom portion. On the other hand, when it is determined that the correlation is high only in the bottom portion, in addition to the roughness of the type of FIG. 1 or 2, it is also considered that a portion around the surface is largely eroded due to the roughness having no correlation between right and left edge roughness due to the cause of (4).

According to the determination criteria, the cause of the edge roughness shown in FIG. 5 was determined as (2) or (7). The observed wafer was sent as a conforming item to the following process, and the inspection was once finished.

Next, a resist pattern formed by different exposure equipment was inspected, the same result as the above was derived. Consequently, the observer determined that there is the higher possibility that (7) is the cause than (2), and the scanning electron microscope was inspected. It was found that the screen of the observing apparatus is distorted due to an influence of the magnetic field generated from a peripheral device. By thoroughly performing shielding against the magnetic field, there became no distortion, and measurement of higher precision could be performed.

Sixth Embodiment

Figure 15:
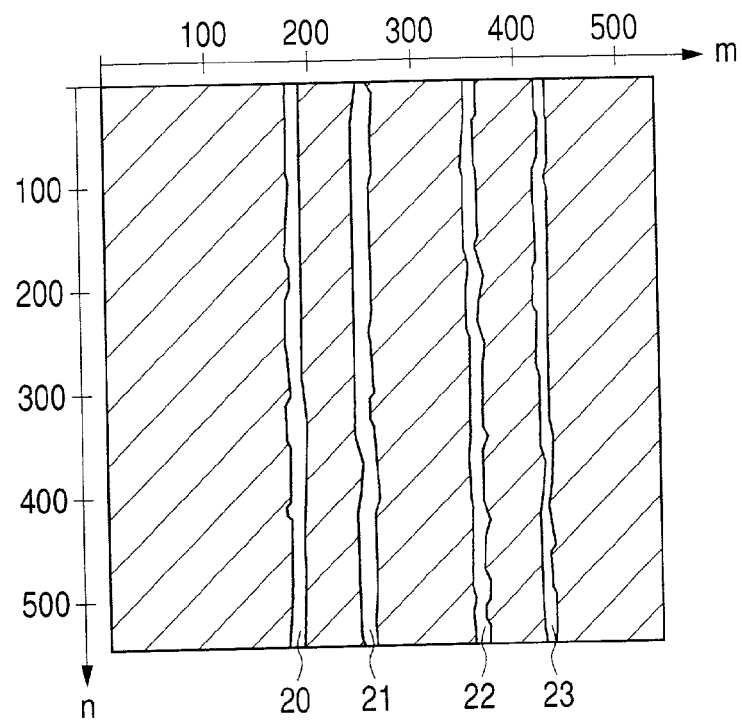
FIG. 15 is a schematic diagram of an observed image which is evaluated in the fifth embodiment of the invention.
Figure 16:
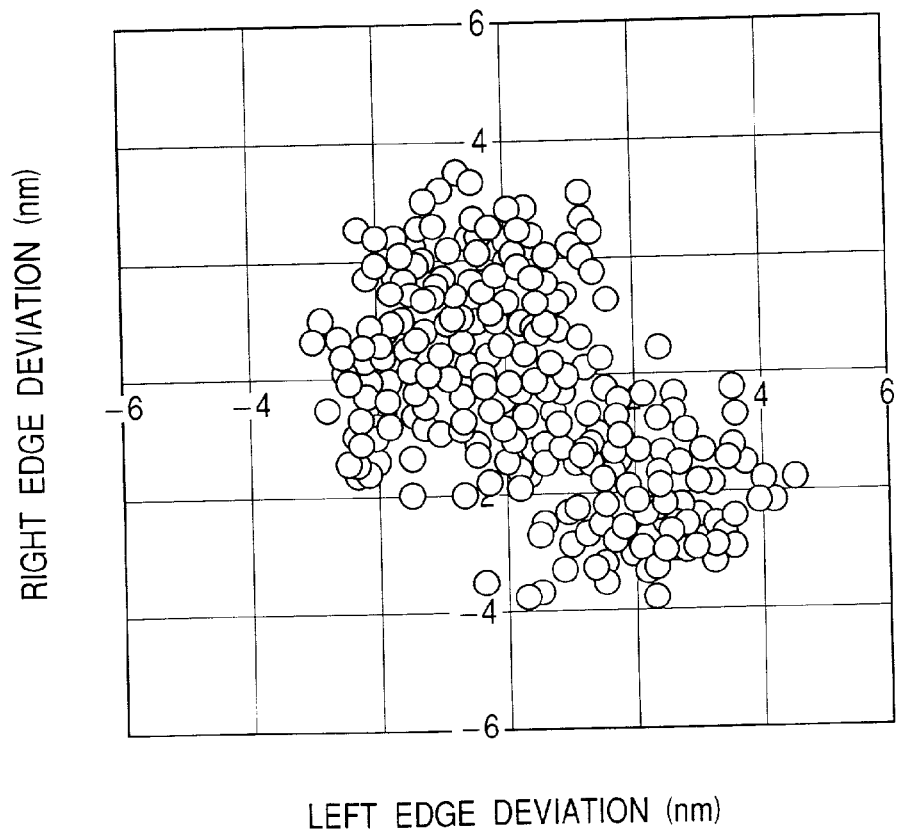
FIG. 16 is a diagram showing threshold parameter dependence of the correlation coefficient of the right and left edge roughness in one line obtained by the fifth embodiment of the invention.

A sixth embodiment of the invention will now be described by referring to FIG. 3 and FIGS. 15 and 16. FIG. 15 is a concept diagram showing an image of data used for evaluation. FIG. 16 is a graph showing the correlation of right and left edge position fluctuations of a line pattern observed.

The pattern shape was evaluated and determined by using the apparatus shown in FIG. 3 in accordance with the same flow as that of the fifth embodiment.

First, by performing an operation from the control system 15 of a scanning electron microscope having a length measuring function, a line pattern of a positive type ArF resist formed on a silicon wafer is observed by ArF lithography on the sample wafer 11. For the purpose of observing edge roughness having a large space period, the magnification is desirably 100,000 times or less. In the example, the observation was made at the magnification of 100,000 times. The line pattern to be observed is mounted in the direction almost perpendicular to the scan direction. The observation area has a length of 1.35 μm in the direction perpendicular to the line pattern and a length of 5.40 μm in the direction parallel to the line pattern, and the distance between neighboring scan lines is 10.55 nm. When the purpose is to observe the presence or absence of fluctuation in edge position of a large space period regarding a narrow line pattern, it is desirable to set the aspect ratio of the observation area to 2:1 or higher. Since the length in the vertical direction of the area to be observed was 6 μm in the example, 4:1 was set. After scanning 64 times, the measurement results of intensity of secondary electrons emitted from the pattern were added up, the average value was used as shades of the gray scale, and the shades were displayed as an image on the screen of the control system 15.

FIG. 15 is a schematic diagram of an image appeared on the screen. The image data is constructed by 512 pixels in the lateral direction and 512 pixels in the vertical direction. It is assumed that the upper left point of the image is the origin, the distance to the right is expressed as (x), and the distance to the left is expressed as (y). The number of each of pixels in the (x) direction is expressed as (m), and the number of each of pixels in the (y) direction is expressed as (n). The area of one pixel has an area having a length of 2.637 nm in the x direction and a length of 10.55 nm in the y direction. In reality, an image having shades according to the intensities of secondary electrons appears. In FIG. 15, areas where the intensity of secondary electrons is high, that is, an edge can exist are expressed in white, and areas in which the intensity of secondary electrons is low are hatched. The coordinates shown in FIG. 15 express the image pixel numbers.

After stopping irradiation of the electron beam to the wafer, the image data was transferred from the control system 15 to the computer 16 adjacent to the control system 15. A program for conducting an inspection according to the invention was executed from a terminal of the computer 16. The program processed an image file converted to the numerical value data of 512×512 pixels by using the threshold method described in the first embodiment, and the coordinates of edge points of total four edges of two lines existing in the image were detected. In consideration of the balance between noise reduction and accuracy, the averaging parameter was set to 4, and the smoothing parameter was set to 3. Calculation was executed on all of profiles, that is, 512 profiles, and the threshold p was set to 0.5. An entered edge retrieval area was set as follows. By eye estimation from the position of an area 20, the area of the left edge of the first line was determined from m=170 to 200. The right edge of the first line was determined from m=230 to 270 on the basis of the position of an area 21. The left edge of the second line was determined on the basis of the position of an area 22 as m=340 to 380. The right edge of the second line was determined on the basis of the position of an area 23 as m=410 to 450.

A set of points indicative of the four edges was approximated by least square with four straight lines $x=ay+b_1$, $x=ay+b_1+w_1$, $x=ay+b_2$, and $x=ay+b_2+w_2$ which are parallel to each other, and the edge point fluctuations were calculated by the same method as that of the first embodiment. For example, a fluctuation in the left edge point of the first line obtained with respect to a profile whose y coordinate is an integer (n) is described as $\Delta x_{1L}(n)$ and a fluctuation in the right edge point is described as $\Delta x_{1R}(n)$. Fluctuations on all of profiles having n of 1 to 512 were calculated.

Next, when whether the sample is good or not was determined, the all of the line edge roughness degree were larger than 6 nm and an alarm sound was generated. The shape analysis was further conducted to see the cause of this large roughness, and only the first and third inspection items described in the fifth embodiment were conducted.

The spatial frequency analysis as the first inspection item was performed on the total four edges of both right and left edges of the first and second lines. The derived graph was displayed on the screen of the computer 16. Subsequently, by a method similar to that in the first embodiment, the intensity A(f) in the area of 15<f<256 was approximated by the function $A_0 \times 1/f$, and the function $A_0 1/f$ for which the obtained fitting parameter $A_0$ was substituted was plotted on the graph. After calculating all the edges, the intensity of the actual measurement value was higher than the approximation value in any cases where f=6, 7, 13, 14, 19, 20, 27, and 34. It means that the line width changes in predetermined cycles, and the cycle is about ⅐ to ⅙ of the length 5.40 μm of the image subjected to the data process.

Next, the third inspection was performed, specifically, the coefficient of correlation of sets of the right and left edge points of one line was calculated. At any of the values p, the coefficient of correlation of the first line lies in the range of ±0.12 of −0.52, and the coefficient of correlation of the second line lies in the range of ±0.14 of −0.45. It was found that there is a strong negative correlation. FIG. 16 shows a graph of the correlation between the right and left edges in the first line when p is 0.5.

The function of determining the roughness causing process was executed here. A warning of an abnormal appearance of a pattern in the underlayer as the cause (6) of roughness described in the fifth embodiment was displayed and an instruction to temporarily stop the lithography process performed on the substrate and make a check was given. The details of the warning were displayed, and the possibility that periodic patterns exist in the underlayer substrate at a pitch of 0.7 to 0.9 μm and cause a unevenness of reflectance was pointed out.

According to the warning, a signal is sent from the computer 16 to a lithography system 17 to stop the lithography process, the processes before the lithography were also temporarily stopped, and the history of the substrate was referred to. It was recognized that metal line patterns exist in the substrate in the direction perpendicular to the line pattern observed, and the pitch of the metal line patterns was 0.8 μm. It is estimated that, in an area on the metal line patterns, antireflection is imperfect, and the line pattern of the resist was consequently narrowed. Based on the estimation, antireflection was thoroughly performed. After that, such a phenomenon stopped appearing, and the yield was improved. By temporarily stopping the processes in response to the warning, the number of wafers going back to fabrication of an antireflection film could be minimized.

Seventh Embodiment

Figure 17:
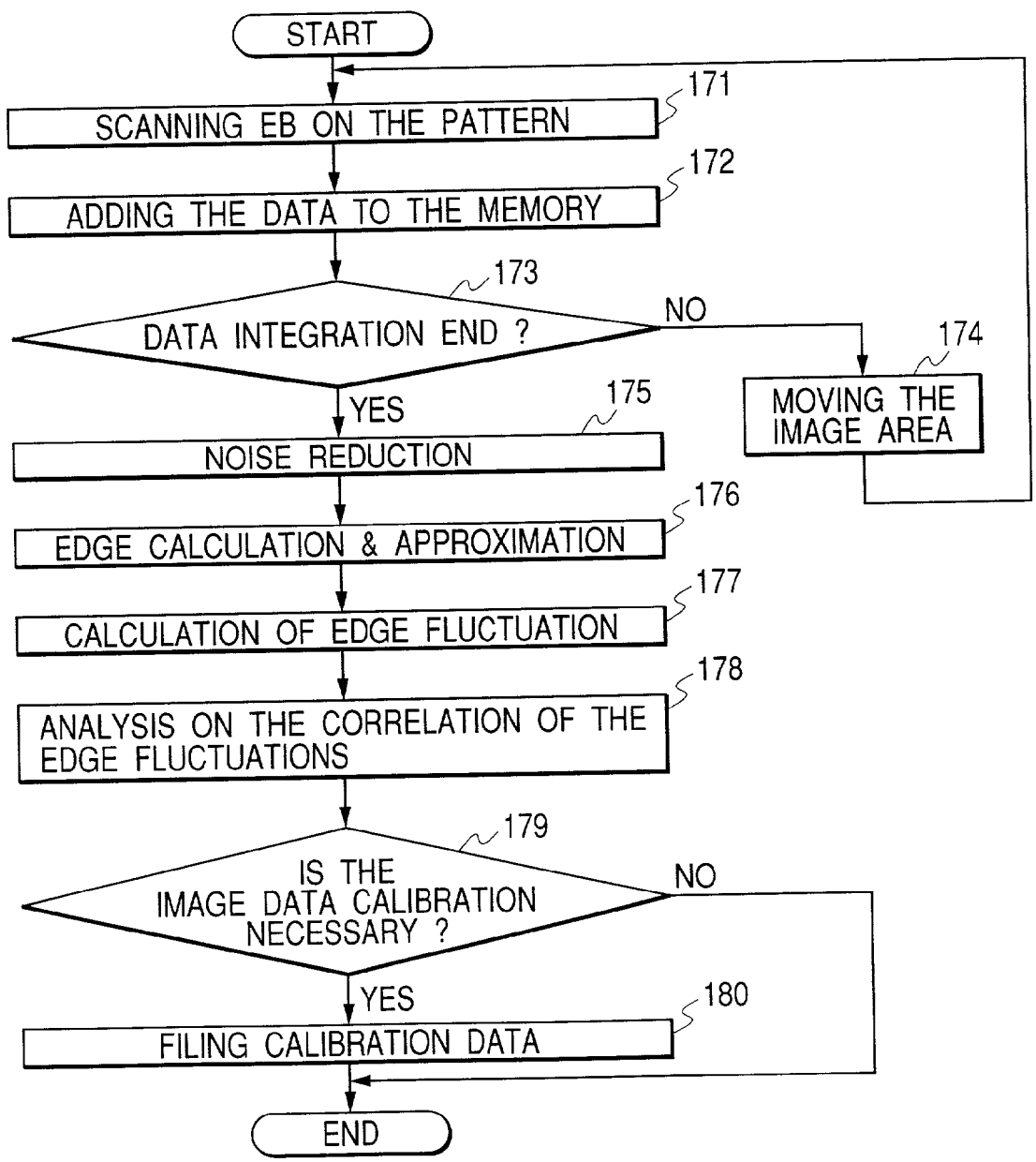
FIG. 17 is a flowchart showing the procedure of a sixth embodiment of the invention.
Figure 18:
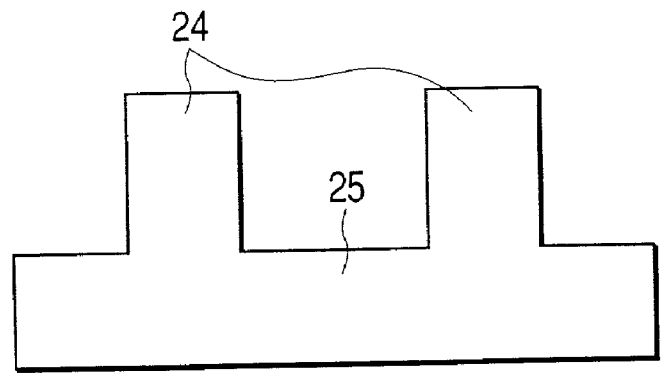
FIG. 18 is a schematic diagram of a structure of a sample observed in the sixth embodiment of the invention.
Figure 19:
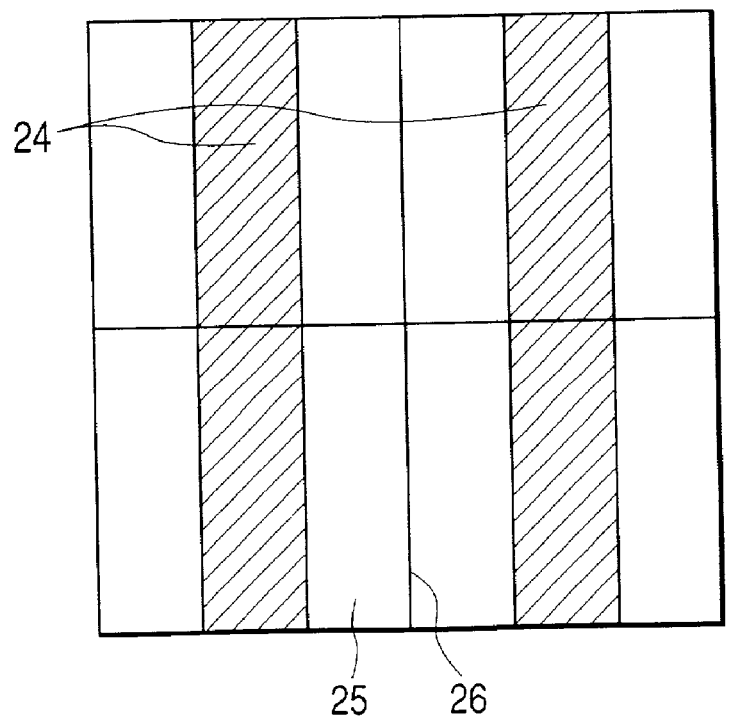
FIG. 19 is a schematic diagram of the observed image evaluated in the sixth embodiment of the invention.
Figure 20:
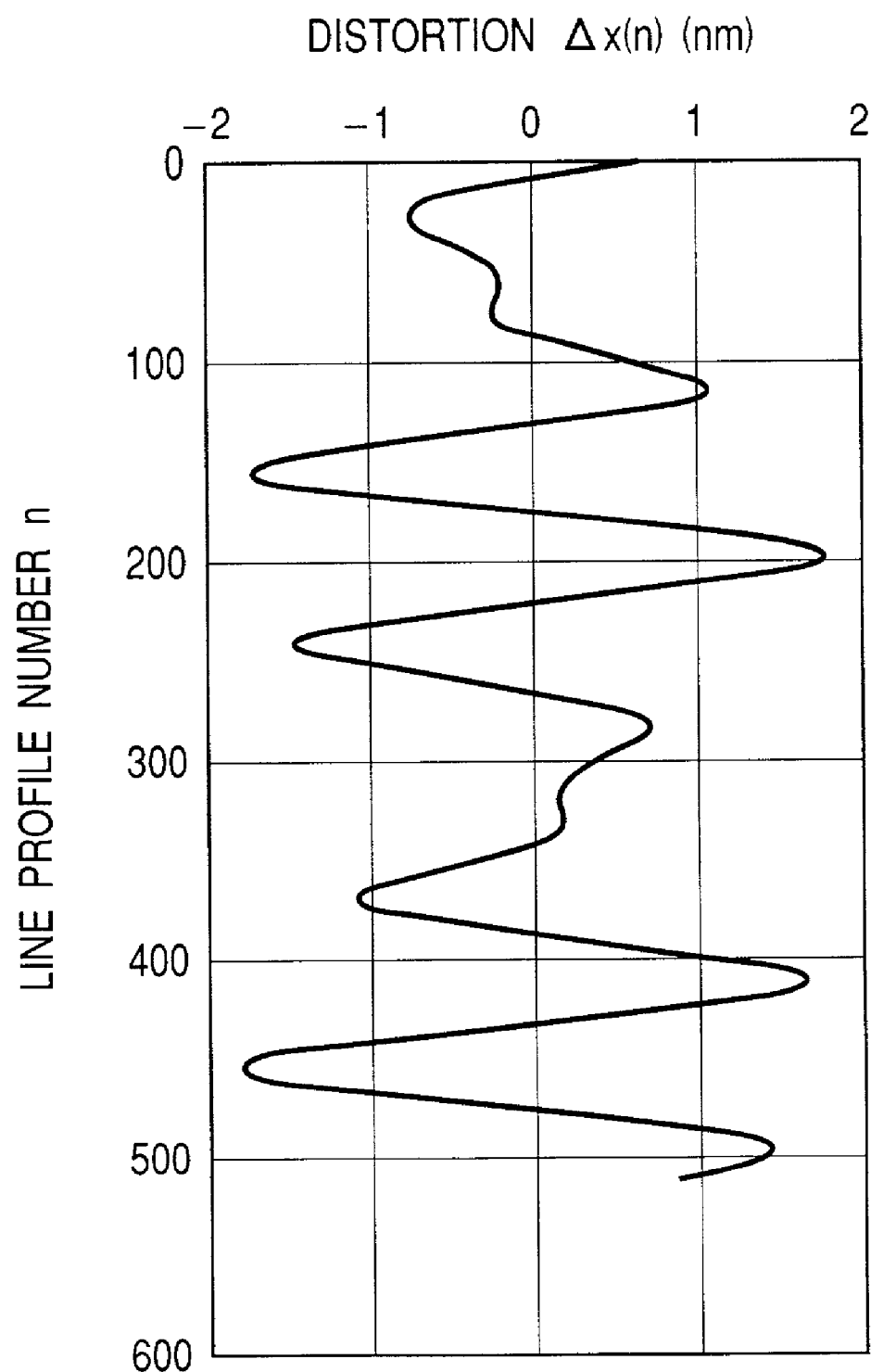
FIG. 20 is a diagram showing an image distortion amount obtained by the sixth embodiment of the invention.

A seventh embodiment of the invention will be described by referring to FIG. 3 and FIGS. 17 to 20. FIG. 17 is a flowchart for acquiring image distortion data. FIG. 18 is a schematic cross section of a sample used. FIG. 19 is a schematic diagram showing the screen of a microscope showing arrangement of the sample at the time of observation. FIG. 20 is a graph showing an image distortion amount obtained.

Detection of distortion and acquisition of data for correction were performed by using the apparatus of FIG. 3 in accordance with the flow of FIG. 17.

First, an operation was performed from the control system 15 of the scanning electron microscope having the length measuring function, and a standard sample made of silicon mounted on the stage 12 of the electron microscope was observed (step 171). The cross section of the structure of the sample is shown in FIG. 18. FIG. 19 is a diagram of the structure observed from above, having a line and space shape. Since the magnification of 100,000 times or higher is desired for measuring edge roughness of a line pattern and it is necessary to observe the edges of at least two line patterns by the method, the pitch of the line-and-space pattern formed on the standard sample is desirably 0.5 μm or less. The ratio of the line width to the space width is desirably 1 or less. In the example, a sample having a pitch of 0.24 μm and the line width of 0.10 μm was used and observed at the magnification of 200,000 times. The area to be observed was a square area of 675×675 nm. The result of observation, that is, the intensity distribution of detected secondary electrons, was displayed as shades of the gray scale on pixels in corresponding portions. The observed area is displayed as an image of 512×512 pixels.

As an initial position, the sample was mounted so that the center of a space part 25 between two lines 24 almost coincides with a vertical axis 26 indicative of the center of the observation area. The edge direction of the line pattern was so arranged to be in parallel with the vertical axis 26 by view observation.

Subsequently, a data accumulating program for detecting distortion was executed.

First, a storage area for taking in image data in the control system 15 in the scanning electron microscope was initialized to set all values to "0". The following first and second procedures were performed repeatedly (corresponding to an operation of performing steps 172 and 174, and returning again to step 171).

First, scanning was performed eight times with the scanning electron microscope, the intensities of secondary electrons emitted from the sample were added up, and the average value was calculated and added to the memory area of the control system (step 172). Second, the irradiation of an electron beam was stopped and a check is made to see whether or not the scan has reached the repetition number of times which has been set (step 173). If "Yes", the program advances to the following step 175. If "No", the scan position is moved upward in the screen by an amount of eight pixels, that is, 10.55 nm (step 174). The number of repetition times was set 128. It took about 40 seconds to integrate 128 average image data of eight scans. Desirably, the number of scans in the first procedure is at least four in order to reduce noise. It is also desirable that observation area of the first time and that of the last time are not overlapped with each other, so that the product between the movement distance in the second procedure and the number of times for repeating the first and second procedures is preferably set to be equal to or larger than the length in the vertical direction of the area which can be observed at a time. In the following, it is assumed that the upper left point of an image is set as an origin, the distance to the right side is (x), and the distance to the below is (y). The numbers of pixels in the x and y directions are expressed by (m) and (n), respectively.

The above process was finished and data of the secondary electron intensity distribution of 512×512 pixels stored in the memory area of the control system 15 was divided by the number of repeating times, thereby obtaining an average value per observation. The program advances to step 175. The obtained 512×512 two-dimensional data array is dealt as data of one image, and noise was reduced by the method described in the first embodiment (step 175). The edge detection and calculation of an approximation line were performed by the threshold method (step 176). The detection was performed on the right and left edges of the first and second lines in an image. Each of the averaging parameter and the smoothing parameter was set to 11. 0.5 was used as the threshold parameter. Detection was performed on all the profiles and 512 edge points were calculated per edge. From the data, a set of edge point fluctuations was obtained (step 177). Further, as a reference, the degree of edge roughness, that is, 3σ was calculated by Expression 1. The program may advance to step 178 without calculating 3σ.

In the example, the purpose was to detect image distortions caused by an influence of an apparatus having a power source disposed near the scanning microscope or a power supply cable. The image distortions appear in an area where the spatial frequency is 20 or lower in an image. When the spatial frequency of 20 is converted to a space period, about 25 pixels are derived. Consequently, numerical values equal to or lower than 25 have to be used as the averaging parameter and the smoothing parameter. The larger the parameters are, the more the noise can be reduced. However, when the parameters are too large, an image is averaged too much as a whole. In consideration of the above, it is desirable to use a value from 7 to 15.

As a result of the processes, data of four edges were obtained. The data of one edge is constructed by position coordinates of the 512 edge points. The edges are not actually existing edges but are obtained by averaging actual edge data in the y direction by the above method. Therefore, roughness which occurs at random in the lines observed is eliminated by the averaging.

However, in reality, the degree 3σ of roughness of the edge data was about 3 to 4 nm. The value is large as a noise, and there is the possibility that the microscope image itself is distorted. From the data, the coefficient of correlation of the right and left edge roughness was computed by the method described in the fourth embodiment, and 0.68 was obtained. The coefficient of correlation of the right and left edge roughness of the second line was also high as 0.55.

The coefficient of correlation between edges belonging to different lines were computed. To be specific, the combinations are (1) the left edges of the first and second lines, (2) the left edge of the first line and the right edge of the second line, (3) the right edge of the first line and the left edge of the second line, and (4) the right edges of the first and second lines. All the coefficients of correlation computed were equal to or higher than 0.5. It means that the whole image is distorted but is seen like a part of the profiles is parallel-translated in the x direction. Consequently, it was determined in step 179 that the image has to be corrected.

Next, the four edge roughness was averaged every profile number and the resultant was used as an image distortion of the microscope itself. FIG. 20 shows a graph of an image distortion amount Δx(n) with respect to an obtained line profile number (n). It is also possible to regard the roughness of an edge close to the center as an image distortion amount without averaging data of the four edges. The data of the image distortion amount obtained was recorded in a file (step 180).

An arbitrary sample was observed at the same magnification, and the image distortion of an obtained profile of the intensity of the secondary electron was corrected with an offset of −Δx(n) When the distortion amount is large, by dividing the offset amount −Δx(n) of each profile by scan speed to calculate offset time and deviating the scan start timing of each profile by the offset time, similar effects are obtained.

In the case of making observation at different observation magnifications, a file of image distortion data Δx(n) at each of the magnifications is generated by the above procedure and, by using the file, an image distortion was corrected by the above method.

Consequently, without thoroughly correcting hardware as did conventionally, the image distortion of the scanning electron microscope is eliminated by a cheap and easy method, and an inspection of high precision can be conducted.

Although observation of a two-dimensional distribution of secondary electrons by a scanning microscope using electron beams has been described as an object in all of the foregoing embodiment, the invention can be also applied to a case using a two-dimensional distribution of particles such as reflected electrons which are emitted secondarily from a sample. The invention can be also applied to cases of observation by a scanning microscope using a charged particle beam such as an ion particle beam or ionizing radiation or, further, light.

As described above, according to the invention, by observing a fine pattern with the scanning microscope, that is, by a non-destructive inspection, the three-dimensional shape of a pattern edge can be expressed in numerical value data. Degree of roughness in the direction along a line, a wavy state of a line, and the difference in the roughness shape between a bottom portion and a portion around the surface of a pattern can be quantitatively expressed.

Further, by analyzing the results, candidates of processes as a main cause of roughness are selected, and the fabricating process of a semiconductor device or a micromachine can be controlled. An image distortion of the microscope itself used for observation can be also extracted and eliminated from an arbitrary image by a simple, cheap method.

According to the invention, the method and apparatus for circuit pattern inspection capable of converting the evaluation of characteristics of edge shape, which is conventionally visually observed, into values, performing analysis quantitatively and promptly with high precision, and specifying the cause of occurrence of roughness systematically can be realized. Further, by using the method and apparatus to control the fabricating process or fabricating apparatus causing the roughness, a super minute patterning process is managed, so that improvements in yield and throughput can be expected.

What is claimed is:

1. A circuit pattern inspection method of inspecting a pattern shape on the basis of two-dimensional distribution information of intensities of secondary electrons or reflected electrons obtained by observing a pattern formed on a substrate by a scanning microscope using a charged particle beam, comprising:
   a step of detecting a set of edge points indicative of positions of line edges of said pattern in a two-dimensional plane from said two-dimensional distribution information by a threshold method;
   a step of obtaining an approximation line for the set of edge points detected for each line edge by least square;
   a step of obtaining an edge roughness shape by calculating the difference between the set of said edge points belonging to each line edge and said approximation line; and
   a step of displaying correlation between edge roughness shapes of different line edges.

2. The circuit pattern inspection method according to claim 1, wherein a plurality of values are used as thresholds used for said threshold method.

3. The circuit pattern inspection method according to claim 2, further comprising a step of calculating a spatial frequency distribution of said edge roughness shape obtained.

4. The circuit pattern inspection method according to claim 2, further comprising a step of obtaining the degree of said edge roughness by calculating a standard deviation expressed by the square root of an average of root-mean-square values of the differences each between the set of said edge points derived with respect to said plurality of thresholds and said approximation line.

5. The circuit pattern inspection method according to claim 2, further comprising a step of selecting a candidate of a process of forming a pattern of said substrate, which causes occurrence of roughness from said edge roughness shape obtained, and displaying the candidate.

6. A circuit pattern inspection method of inspecting a pattern shape on the basis of two-dimensional distribution information of intensities of secondary electrons or reflected electrons obtained by observing a pattern formed on a substrate by a scanning microscope using a charged particle beam, comprising:
   a step of detecting a set of edge points indicative of positions of edges of said pattern in a two-dimensional plane from said two-dimensional distribution information by a threshold method;
   a step of obtaining an approximation line for the set of edge points belonging to said edge detected;
   a step of obtaining an edge roughness shape by calculating the difference between the set of said edge points and said approximation line; and
   a step of selecting a candidate of a pattern forming process on said substrate as a cause of occurrence of roughness from said edge roughness shape obtained and displaying the candidate,
   wherein a plurality of values are used as thresholds used for said threshold method.

* * * * *